(12) United States Patent
Paielli et al.

(10) Patent No.: US 9,334,950 B2
(45) Date of Patent: May 10, 2016

(54) DIFFERENTIAL CARRIER ELECTRONICS PACKAGE

(71) Applicant: Dana Automotive Systems Group, LLC, Maumee, OH (US)

(72) Inventors: Perry M. Paielli, Commerce Township, MI (US); Michael Z. Creech, Ann Arbor, MI (US)

(73) Assignee: Dana Automotive Systems Group, LLC, Maumee, OH (US)

( * ) Notice: Subject to any disclaimer, the term of this patent is extended or adjusted under 35 U.S.C. 154(b) by 182 days.

(21) Appl. No.: 14/197,684

(22) Filed: Mar. 5, 2014

(65) Prior Publication Data

US 2014/0254102 A1    Sep. 11, 2014

Related U.S. Application Data

(60) Provisional application No. 61/775,929, filed on Mar. 11, 2013, provisional application No. 61/775,959, filed on Mar. 11, 2013.

(51) Int. Cl.
*F16H 61/00*      (2006.01)
*G01N 25/72*      (2006.01)
(Continued)

(52) U.S. Cl.
CPC ............ *F16H 61/0006* (2013.01); *F16H 59/72* (2013.01); *G01N 25/72* (2013.01); *F16H 57/0405* (2013.01); *H05K 7/20854* (2013.01)

(58) Field of Classification Search
CPC .. F16H 61/0006; F16H 59/72; F16H 57/0405
USPC ........................ 361/679.46–679.54, 688–723; 165/80.2, 80.4–80.5, 104.33; 257/712–714, 721; 174/547–548; 74/606 A
See application file for complete search history.

(56) References Cited

U.S. PATENT DOCUMENTS

| 5,662,007 A * | 9/1997 | Starker | F16H 57/04 74/606 A |
| 6,688,383 B1* | 2/2004 | Sommer | F16H 57/0412 123/41.34 |

(Continued)

FOREIGN PATENT DOCUMENTS

| DE | 10016640 C1 | 9/2001 |
| EP | 1508915 A2 | 2/2005 |

(Continued)

OTHER PUBLICATIONS

International Search Report with Written Opinion—PCT/US2014/021547.

(Continued)

*Primary Examiner* — Zachary M Pape
(74) *Attorney, Agent, or Firm* — Marshall & Melhorn, LLC

(57) ABSTRACT

A differential carrier electronic package has a package housing that is made of upper and lower portions that are sealed together, where the upper portion has high thermal conductive properties and the lower portion has low thermal conductive properties. The upper and lower portions are in thermal contact with an environment that is external to a differential carrier housing. The lower portion extends through an opening in the differential housing, thereby further being in thermal contact with a fluid within the differential housing. The package housing further has an electronic circuit that is attached to and in thermal conduction with the upper portion, within the package housing. The lower portion may have a connector portion formed in it for electrically connecting between external electrical devices and sources, the electronic circuit, and control devices within the differential housing.

13 Claims, 1 Drawing Sheet

(51) Int. Cl.
*F16H 59/72* (2006.01)
*H05K 7/20* (2006.01)
*F16H 57/04* (2010.01)

(56) References Cited

U.S. PATENT DOCUMENTS

| | | | |
|---|---|---|---|
| 7,624,660 B2* | 12/2009 | Morise | F16H 57/0421 |
| | | | 184/6.12 |
| 8,059,407 B2* | 11/2011 | Eglinger | B60R 16/0239 |
| | | | 361/679.01 |
| 8,792,242 B2* | 7/2014 | Wetzel | H05K 5/0082 |
| | | | 361/707 |
| 2006/0054411 A1 | 3/2006 | Fett et al. | |
| 2008/0029875 A1* | 2/2008 | Zhuang | H01L 23/04 |
| | | | 257/691 |
| 2009/0062164 A1* | 3/2009 | Hee | C10M 101/02 |
| | | | 508/110 |
| 2011/0228478 A1* | 9/2011 | Takata | F16H 61/0006 |
| | | | 361/699 |
| 2012/0103132 A1* | 5/2012 | Morris | F16H 61/0006 |
| | | | 74/606 R |
| 2014/0254623 A1* | 9/2014 | Paielli | G01N 25/72 |
| | | | 374/10 |
| 2014/0318296 A1* | 10/2014 | Zweigle | F16H 61/0006 |
| | | | 74/473.12 |

FOREIGN PATENT DOCUMENTS

| | | |
|---|---|---|
| EP | 1637847 A1 | 3/2006 |
| EP | 2482050 A2 | 8/2012 |
| WO | 9928149 A1 | 6/1999 |
| WO | 2012074112 A1 | 6/2012 |

OTHER PUBLICATIONS

Communication Relating to Results of Partial International Search—PCT/US2014/021519.
English Language Abstract—DE10016640.

* cited by examiner

DIFFERENTIAL CARRIER ELECTRONICS PACKAGE

RELATED APPLICATION

This application claims the benefit under 35 U.S.C. §119 (e) of U.S. Provisional Patent Application Ser. Nos. 61/775,929 and 61/775,959, both of which were filed on Mar. 11, 2013 and are incorporated by reference herein in their entirety.

FIELD OF THE INVENTION

The present invention relates to packaging for electronic controls within an extreme environment application. More particularly, the present invention relates to packaging for electronic controls within the extreme environment of a vehicle differential carrier.

BACKGROUND OF THE INVENTION

A vehicle differential is a device employing differential gears within a housing called a differential carrier. The vehicle differential is connected to three shafts. An input shaft transmits torque and rotation from a vehicle engine into the differential gears. In turn, each of the other two shafts separately transmits a portion of the torque and rotation from the differential gears out to separate external wheels.

For lubrication of the meshing of the differential gears, the differential gears within the differential carrier are at least partially submerged in a lubricant, for example, a mineral— standard base lubricant or a synthetic—premium lubricant. In either case, the lubricant may be certified as an API GL5 classification oil or SAE J2360 standard oil, and sealed within the differential carrier housing.

As a result of initial machining of the differential and associated parts therein, along with rigorous meshing of the differential gears during the differential's operation over an extended period of time, metal particles enter the lubricant within the differential and cause friction within. In turn, the friction affects the thermal conditions by increasing the temperature within the differential, which in turn causes more wear on the associated parts.

In general, when the rear wheels of a vehicle are caused to turn or are experiencing wheel slippage, as quite often happens, an outside wheel(s) makes a larger radius than an inside wheel(s). As a result, the outside wheel goes a farther distance, moves faster, and turns more revolutions than the inside wheel. Consequently, when both wheels are on the same axle shaft, one or both wheels would have to skid or slip to make a turn. However, by applying a differential between the rear wheels, the wheels are allowed to turn at different speeds.

As a vehicle operates, the meshing and rotation of differential gears, along with the presence of metal particles in the oil of the differential, friction increases. This results in heat building up within the space, oil, and parts that comprise the differential. Consequently, the differential experiences temperature swings and potentially extreme operational temperatures that can lead to part failures. Hence, it would advantageous to know the thermal conditions within the differential carrier, in order to detect potential part failures and long term reliability problems.

Even with these extreme conditions it is necessary to control and sense various solenoids, actuators, and sensors that are disposed on or within the differential carrier, which are used as locking mechanisms, fluid flow control valves, and clutch mechanisms. Unfortunately, electronic circuits that are needed to control such solenoids, actuators, and sensors cannot withstand being conventionally mounted on differential carriers, where they would be needed. This results in reducing or even eliminating the effectiveness of such controls.

Consequently, it would be beneficial to provide a means to monitor the thermal conditions within a differential, while using a packaging with standard electronic controls therein that would be able to function properly at or even within the extreme conditions presented by a differential carrier. Such a monitoring means needs to be directed to electronic controls that would include sensing solenoids, actuators, sensors, and the like that are disposed on or within a differential carrier.

SUMMARY OF THE INVENTION

A differential carrier electronics package is used at and within a vehicle differential carrier that comprises a package housing, which comprises an upper portion and a lower portion that are sealed together, where the upper portion has high thermal conductive properties and the lower portion has thermally insulating properties. The upper portion and the lower portion are in thermal contact with an environment that is external to the differential carrier housing. The lower portion is also in thermal contact with an outer surface of the differential carrier housing, where the lower portion of the package housing extends through an opening in the differential housing, thereby further being in thermal contact with a fluid within the differential housing. However, no part of the upper portion is in contact with the fluid. The fluid may be in a form of a liquid and/or vapor. The package housing further comprises an electronic circuit. The electronic circuit is attached to and in thermal conduction with the upper portion, within the package housing.

By way of the electronic circuit, first connector pins extend from the electronic circuit and then into the connector housing of the differential housing lower portion, thereby allowing the electronic circuit to be externally electrically connected to devices and power sources. Also, second connector pins extend from the electronic circuit and then out through a bottom of the lower portion of the differential housing and into the fluid within the differential carrier housing, thereby allowing the electronic circuit to be internally electrically connected to devices within the differential carrier.

Further objects and advantages of the present invention will be apparent from the following description and appended claims, reference being made to the accompanying drawings forming a part of a specification, wherein like reference characters designate corresponding parts of several views.

DESCRIPTION OF THE INVENTION

Figure 1:
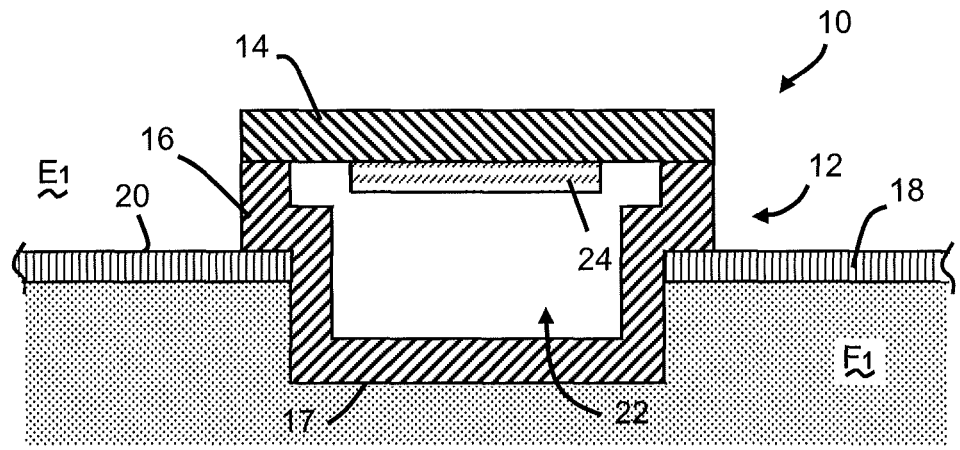
FIG. 1 is a cross sectional view of a first differential carrier electronics package in accordance with the present invention.

It is to be understood that the invention may assume various alternative orientations and step sequences, except where expressly specified to the contrary. It is also to be understood that the specific devices and processes illustrated in the attached drawings, and described in the following specification are simply exemplary embodiments of the inventive concepts defined in the appended claims. Hence, specific dimen- FIG. 1 illustrates a first embodiment of a differential carrier electronics package 10 having a protective package housing 12 that comprise an upper portion 14 and a lower portion 16 that are sealed together, where the upper portion 14 has high thermal conductive properties and the lower portion 16 has thermally insulating properties. The upper portion 14 would comprise a thermally conductive metal, for example, aluminum and the lower portion 16 would comprise a thermally insulating high-temperature plastic.

The two package portions 14, 16 may be unitary, with one another. The upper portion 14 and the lower portion can be sealed together by way of adhesives, mechanical means like screws and clamps, injection molding therebetween, and other standard means.

The upper portion 14 and the lower portion 16 are in direct thermal contact, as indicated in FIG. 1, with an environment $E_1$ that is external to a differential carrier housing 18. The lower portion 16 is also in direct thermal contact with an outer surface 20 of the differential housing 18, as indicated in FIG. 1, where the lower portion 16 of the package housing 12 extends through an opening 22 in the differential housing 18. Thereby, the differential carrier electronics package 10 allows the lower portion 16 to be in direct thermal contact with a fluid $F_1$ within the differential housing 18. The fluid $F_1$ may be in a form of a liquid and/or vapor. The package housing 12 further comprises an electronic circuit 24. The electronic circuit 24 is in thermal contact with and attached to the upper portion 14 within the package housing 12. The electronic circuit 24 is capable of easily thermally conducting heat away from or into the differential carrier electronics package 10.

Figure 2:
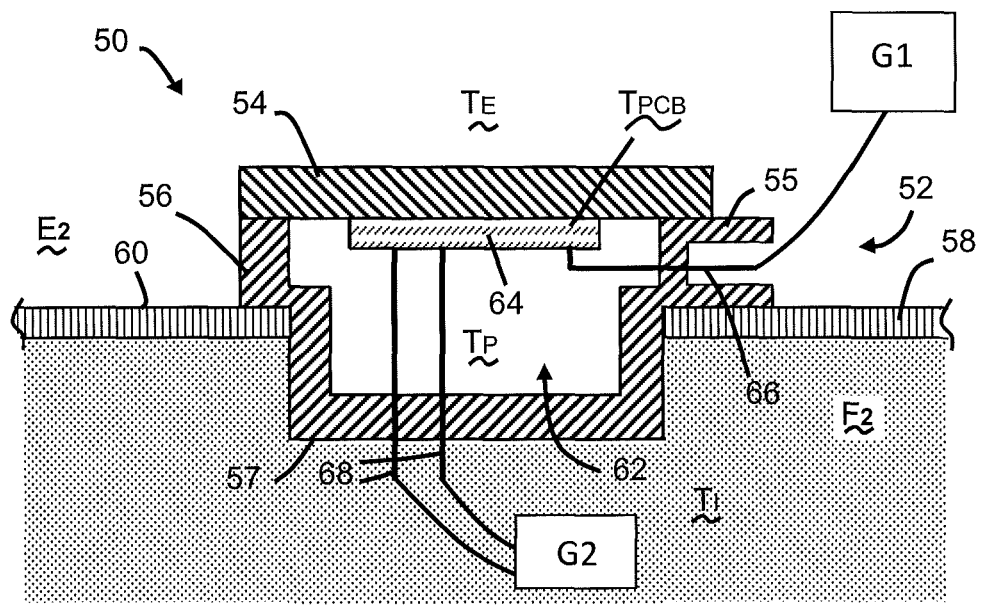
FIG. 2 is a cross sectional view of a second differential carrier electronics package in accordance with the present invention.

Although the lower portion 17 material is a poor thermal conductor, the upper portion 14 temperature is close to outside ambient temperature $T_E$, as shown in FIG. 2. Also, since the electronic circuit 24 is a good conductor and is well coupled to the upper portion 14, then the difference in temperature between the electronic circuit 24 and the upper cover 14 is small. Consequently, the temperature $T_{PCB}$ of the electronic circuit 24 is approximately equal to the temperature $T_E$ of the exterior of the differential carrier electronics package 10 above the upper portion 14. As a result, the internal package volume temperature $T_P$ is proportional to the ratio of the product of the thermal resistance and area of the upper portion 14 to that of the lower portion 16 exposed to the interior of the differential carrier 18, as detailed in both the related U.S. Provisional Application No. 61/775,929 and its non-provisional application that are incorporated by reference herein, in their entirety. Hence, the temperature difference between the lower portion 16 and the internal temperature $T_P$ is high owing to the low thermal conduction of the lower portion 16 material relative to the upper portion 14 material.

Thereby, the differential carrier electronics package 10 allows for safe and accurate sensing and controlling conditions within the differential carrier housing 18, while allowing the use of standard electronic components and allowing easier integration into the differential carrier electronics package 10.

In a second embodiment, a differential carrier electronics package 50 comprises a package housing 52 that comprises an upper portion 54 and a lower portion 56 that are sealed together by means like those stated-above for the upper and lower portions 14, 16 of the first embodiment. The two package housing portions 54, 56 may be unitary. The upper portion 54 and the lower portion 56 are in thermal contact with an environment $E_2$ that is external to a differential carrier housing 58. However, the upper portion 54 is significantly more capable of conducting heat (e.g., a thermally conductive metal like aluminum) to and from the environment $E_2$ than the lower portion 56 (e.g., thermally low-conductive high-temperature plastic), since the upper portion 54 is much more thermally conductive than the lower portion 56.

The lower portion 56 further comprises a connector housing 55 that is unitary therewith. The lower portion 56 is also in thermal contact with an outer surface 60 of the differential housing 58, where the lower portion 56 of the package housing 52 extends through an opening 62 in the differential housing 58, thereby further being in thermal contact with a fluid $F_2$ within the differential housing 58. The fluid $F_2$ may be in a form of a liquid and/or vapor.

The package housing 52 further comprises an electronic circuit 64. The electronic circuit 64 is attached to and in thermal conduction with the upper portion 54, within the package housing 52. First connector pins 66 extend from the electronic circuit 64 and then into the connector housing 55 of the differential housing lower portion 56, thereby allowing the electronic circuit 64 to be externally electrically connected to common in the art devices and power sources (exterior group G1). Also, second connector pins 68 extend from the electronic circuit 64 and then out through a bottom 57 of the lower portion 56 of the differential housing 58 and into the environment $F_2$ within the differential housing 58, thereby allowing the electronic circuit 64 to be electrically connected to common in the art solenoids, actuators, and sensors (interior group G2) within the differential carrier housing 58.

The upper portion 54 and the lower portion can be sealed together by way of injection molding, adhesives, mechanical means like screws and clamps, and other standard means. The connectors 66, 68 can be held in place and sealed by way of being injection molded into the housing 55, 56.

Hence, internal conditions within a differential carrier housing 58 can be monitored by, for example, an external vehicle electronic control unit (VECU) G1 by way of the first connector pins 66, the electronic circuit 64 within the package housing 52, and then the solenoids, actuators, and sensors G2 that are within the differential carrier housing 58.

As a result of the above-described disclosure, the differential carrier electronics packages 10, 50, upper portions 14, 54, and electronic circuits 24, 64 will easily dissipate heat that builds up within the packages 10, 50, thereby allowing the use of standard electronic components in the extreme environment of the differential carriers 18, 58. In turn, this allows for control and measuring of live conditions, for example, thermal conditions, within the differential carriers 18, 58. Such a controlling and measuring of these live conditions, results in more accurate and reliable information for operating a vehicle, with a better quality differential carrier that is more reliable.

In accordance with the provisions of the patent statutes, the principles and modes of operation of this invention have been described and illustrated in its preferred embodiments. However, it must be understood that the invention may be practiced otherwise than specifically explained and illustrated without departing from its spirit or scope.

What is claimed is:

1. A differential carrier electronics package comprising:
a package housing comprising an upper portion having thermally conductive properties and a lower portion having thermally insulating properties, the upper and lower portions being sealed together;
wherein separately, the upper portion and lower portion being in direct thermal contact with an environment external to a differential carrier housing and the lower portion separately extended through an opening in the differential carrier housing and in thermal contact with a fluid within the differential carrier housing; and wherein no part of the upper portion is in contact with the fluid.

2. The differential carrier electronics package of claim 1, wherein the upper and lower portions of the package housing are unitary.

3. The differential carrier electronics package of claim 1, further comprising an electronic circuit separately attached to and in thermal conduction with the upper portion, within the package housing.

4. The differential carrier electronics package of claim 3, further comprising a lower portion connector housing unitary with the package housing and having first connector pins extended from the electronic circuit into the lower portion connector housing and connected externally electrically to external devices and power sources.

5. The differential carrier electronics package of claim 4, wherein second connector pins extend from the electronic circuit and out through a bottom of the lower portion and into an environment within the differential carrier housing, and electrically connected to devices within the differential carrier housing.

6. The differential carrier electronics package of claim 5, wherein the devices electrically connected by way of the second connector pins, within the differential carrier housing, are selected from a group consisting of solenoids, actuators, and sensors that control mechanisms within the differential carrier housing.

7. The differential carrier electronics package of claim 6, wherein an external vehicle electronic control unit controls the mechanisms within the differential carrier.

8. The differential carrier electronics package of claim 7, wherein the mechanisms within the differential carrier housing are selected from a group consisting of a locking mechanism, fluid flow control valve, and clutch.

9. The differential carrier electronics package of claim 1, wherein the differential carrier fluid is selected from a group consisting of a mineral—standard base lubricant and a synthetic—premium lubricant.

10. The differential carrier electronics package of claim 1, wherein the differential carrier fluid is certified from a group consisting of an API GL5 classification oil and SAE J2360 standard oil.

11. The differential carrier electronics package of claim 1, wherein the upper portion comprises a thermally conductive metal.

12. The differential carrier electronics package of claim 11, wherein the thermally conductive metal comprises aluminum.

13. The differential carrier electronics package of claim 1, wherein the lower portion comprises a thermally insulating high-temperature plastic.

* * * * *